(12) United States Patent
Weilandt et al.

(10) Patent No.: US 6,196,978 B1
(45) Date of Patent: Mar. 6, 2001

(54) IMPACT-DAMPED BIOPSY INSTRUMENT (75) Inventors: Anders Weilandt, Sollentuna; Mikael Lindgren, Upplands Väsby, both of (SE)

(73) Assignee: Ascendia AB, Sollentuna (SE)

( * ) Notice: Subject to any disclaimer, the term of this patent is extended or adjusted under 35 U.S.C. 154(b) by 0 days.

(21) Appl. No.: 09/404,785

(22) Filed: Sep. 24, 1999

Related U.S. Application Data (60) Division of application No. 09/090,908, filed on Jun. 5, 1998, now Pat. No. 6,126,617, which is a continuation-in-part of application No. 08/783,204, filed on Jan. 14, 1997, now Pat. No. 5,788,651, which is a division of application No. 08/378,402, filed on Jan. 26, 1995, now Pat. No. 5,655,542.

(51) Int. Cl.[7] .................................................. A61B 5/00
(52) U.S. Cl. ............................................................. 600/567
(58) Field of Search ........................... 600/562, 564–567; 606/167, 170

(56) References Cited

U.S. PATENT DOCUMENTS

| | | | |
|---|---|---|---|
| 5,156,160 | * 10/1992 | Bennett | 128/754 |
| 5,188,118 | * 2/1993 | Terwilliger | 128/753 |
| 5,282,476 | * 2/1994 | Terwilliger | 128/753 |
| 5,535,755 | * 7/1996 | Heske | 128/754 |

* cited by examiner

*Primary Examiner*—Max Hindenburg
(74) *Attorney, Agent, or Firm*—Ostrolenk, Faber, Gerb & Soffen, LLP (57) ABSTRACT

A biopsy instrument includes a canula slidingly disposed in a finger tube having a finger at its distal end. By forward displacement of the finger tube relative to the canula the finger is inserted into an opening in the canula wall near its cutting front edge. Thereby a piece of tissue located inside the canula is severed from living tissue. The instrument has a steel spring compressed against a force of at least 35 N for displacing the canula and the finger tube in the tissue cutting step. The stopper on which the moving canula impacts includes an element of an impact damping design. The impact damping element is made of high-impact grade ABS-polymer or a polymer with similar physical properties. It can be used also with known biopsy instruments having a moving canula and/or stylet driven by a powerful spring. Also described is a loading assembly for a biopsy apparatus incorporating the biopsy instrument.

8 Claims, 12 Drawing Sheets

IMPACT-DAMPED BIOPSY INSTRUMENT

This is a division of application Ser. No. 09/090,908, filed Jun. 5, 1998, now U.S. Pat. No. 6,126,617 which is a continuation-in-part of application Ser. No. 08/783,204, filed Jan. 14, 1997, now U.S. Pat. No. 5,788,651, which is a division of application Ser. No. 08/378,402, filed Jan. 26, 1995, now U.S. Pat. No. 5,655,542, issued Aug. 12, 1997.

BACKGROUND OF THE INVENTION

1. Field of the Invention

The present invention relates to a biopsy instrument, and to methods and apparatus for collecting tissue samples or the like from humans or animals, in particular by excising a segment from a tissue, using the biopsy instrument. The invention also relates to a loading assembly for a biopsy instrument and an impact damping element for biopsy instruments.

2. Description of the Related Art

The invention departs from an apparatus for collecting tissue samples by excising a segment from tissue, and a corresponding method for harvesting of tissue samples described in U.S. Pat. No. 5,655,542 (Weilandt), the entire disclosure of which is incorporated by reference into this specification.

In this specification, the terms "proximal" and "distal" are used with respect to the person extracting a biopsy sample. Thus, the proximal end of a biopsy apparatus is its rear end, proximate the practitioner, and pointing away from the patient.

The biopsy instrument of the '542 patent includes a first part having an end with means for penetrating a tissue at the end, and a wall having an opening extending through the wall of the first part; and a second part adapted for being slidingly disposed on the first part, excision means for separating a segment of the tissue then penetrated by the first part provided on the second part such that sliding movement of the second part on the first part in one direction causes the excision means to pass through the opening in the wall of the first part thereby separating a segment of the tissue for extraction.

The method of harvesting biopsy samples of the '542 patent includes the steps of injecting the biopsy instrument into tissue to a position proximal of a sample to be taken; displacing simultaneously the first part and the second part of the biopsy instrument for reception of the sample in the first part; displacing the second part to sever the sample from the tissue.

The first part may take the form of a canula and the second part that of a tube in which the canula is slidingly arranged. The tube is provided with a finger at its distal end, the finger entering an opening in the canula wall in the tissue-severing step when the tube is displaced in a distal direction with respect to the canula.

The joint displacement of the first part and the second part following the injection step is accomplished by spring means, in particular a steel coil. Compression steel coils have been found to work well in practice, except for very powerful springs providing high acceleration to the combination of the first and the second part. High acceleration is attractive since, thereby, the use of separate driving force for the second step becomes superfluous, the displacement of the second part with respect to the first part being accomplished through the inertia of the second part. Moreover, high acceleration allows for less variation in sample quality when using the instrument with a variety of tissues. The loading of a biopsy instrument provided with powerful spring means which have to be compressed in the loading procedure constitutes another problem.

SUMMARY OF THE INVENTION

The present invention provides a biopsy instrument that can be reliably driven by strong spring means. The invention also provides a means for damping the impact of a stylet or canula in a biopsy instrument. In addition, the invention provides a loading assembly for loading a biopsy instrument, in particular one with a powerful compression spring.

The invention is a biopsy instrument of the aforementioned kind including means for damping oscillations of the first part with respect to the second part arising from the sudden stop of the first part at the end of the first step when hitting a stopper and that of the second part at the end of the second step. On impact the thin-walled tubiform first and second parts become elongated in their axial direction. In general the canula and the finger tube of electropolished steel have very thin walls of from about 0.05 to 0.1 mm thick while their length varies from about 15 to about 20 cm.

In experiments with strong steel coils, oscillations of amplitudes of up to 1.15 mm were observed. In addition, the first and second part do not necessarily oscillate in phase; they may even oscillate in opposite phase. Undampted, the oscillations often damaged the finger, resulting in incomplete severing of the sample or breakage of the finger. The damage occurs by the finger hitting the distal rim of the opening in the tube wall. Thereby the finger is excessively bent or broken.

According to the present invention, oscillation damping means are provided by appropriate design of the stopper stopping the movement of the first part. With reference to the preferred embodiment of the '542 patent, the first stopping element is the plunger stop 960 modified according to the teaching of the present invention. By using a powerful steel compression spring the actuator coil 94 can be dispensed with. The displacement of the second part in relation to the first part then is caused entirely by inertia.

It is preferred for the steel coil of the biopsy instrument to exert a force of 35 N and more in a compressed state. Particularly preferred is a coil exerting a force of at least 50 N, most preferred of at least 65 N.

A reduction of oscillation by damping so as to keep oscillation of the first part with respect to the second part below 0.4 mm provides a satisfactory result and is preferred. Even more preferred is to keep oscillation within 0.35 mm, even within 0.30 mm and less.

A biopsy instrument according to the invention combines a powerful steel compression spring of the kind described above, an impact damping means to reduce oscillation of a canula with respect to a finger tube slidingly disposed on the canula arising on impact of the canula holder on a stopper, and a design dispensing with the use of spring means to displace the finger tube in a distal direction after the canula has been stopped by the stopper.

The impact damping means of the invention can also be advantageously applied to stop (decelerate) canulas and stylets in biopsy instruments other than that of U.S. Pat. No. 5,655,542, in particular canulas and stylets accelerated by a powerful compression spring, such as one which can be compressed to more than 35 N, preferably more than 50 N, most preferred more than 65 N. The damping means of the invention preferably constitutes an acrylonitrile-butadienestyrene copolymer (ABS) having a yield tensile strength above 35 Mpa and an Izod impact strength of more than 325 J/m, or any other medical grade polymer or other material meeting these requirements.

The loading assembly of a biopsy apparatus incorporates, in a housing, the biopsy instrument according to the invention includes a loading arm swivellingly attached at its one end to the housing, an intermediate arm swivellingly attached at its one end to the loading arm and at its other end to a catch holding the canula holder during tensioning and in a tensioned position with respect to a tension spring or during compression, or in a compressed position with respect to a compression spring (the latter being preferred). The catch is displaceable in a proximal direction against the resistance of the spring and is adapted to be held there for intentional release. It is obvious that this loading assembly can also be advantageously used for tensioning or compressing spring means arranged for displacement of one or several elements of a biopsy apparatus different from that of the invention.

BRIEF DESCRIPTION OF THE DRAWINGS

Further advantages of the present invention will become obvious from the study of a preferred but not limiting biopsy instrument and a corresponding apparatus according to the invention which is illustrated in a drawing of which the individual figures are described briefly as follows.

Indications of lateral direction such as 'from above', 'underside', 'top side' are defined by the view of FIGS. 8–11. The steel coil compression spring is only shown in FIG. 8.

DETAILED DESCRIPTION OF THE PREFERRED EMBODIMENTS

The biopsy instrument illustrated in FIGS. 1–7 includes a canula 101, a finger tube 201, and a stylet 301 of the same kind as in U.S. Pat. No. 5,655,542, where the design and function of these elements is explained in detail and thus need not be repeated here. In some of the figures of the present specification rear (proximal) end portions of the canula 101, the finger tube 201, and the stylet 301 are shown to illustrate their relationship with their respective holders 100, 200, 300, each made in one piece of a polymer material, preferably an ABS polymer (acrylonitrile-butadiene-styrene copolymer) or another polymer of high impact and tensile strength.

Figure 1:
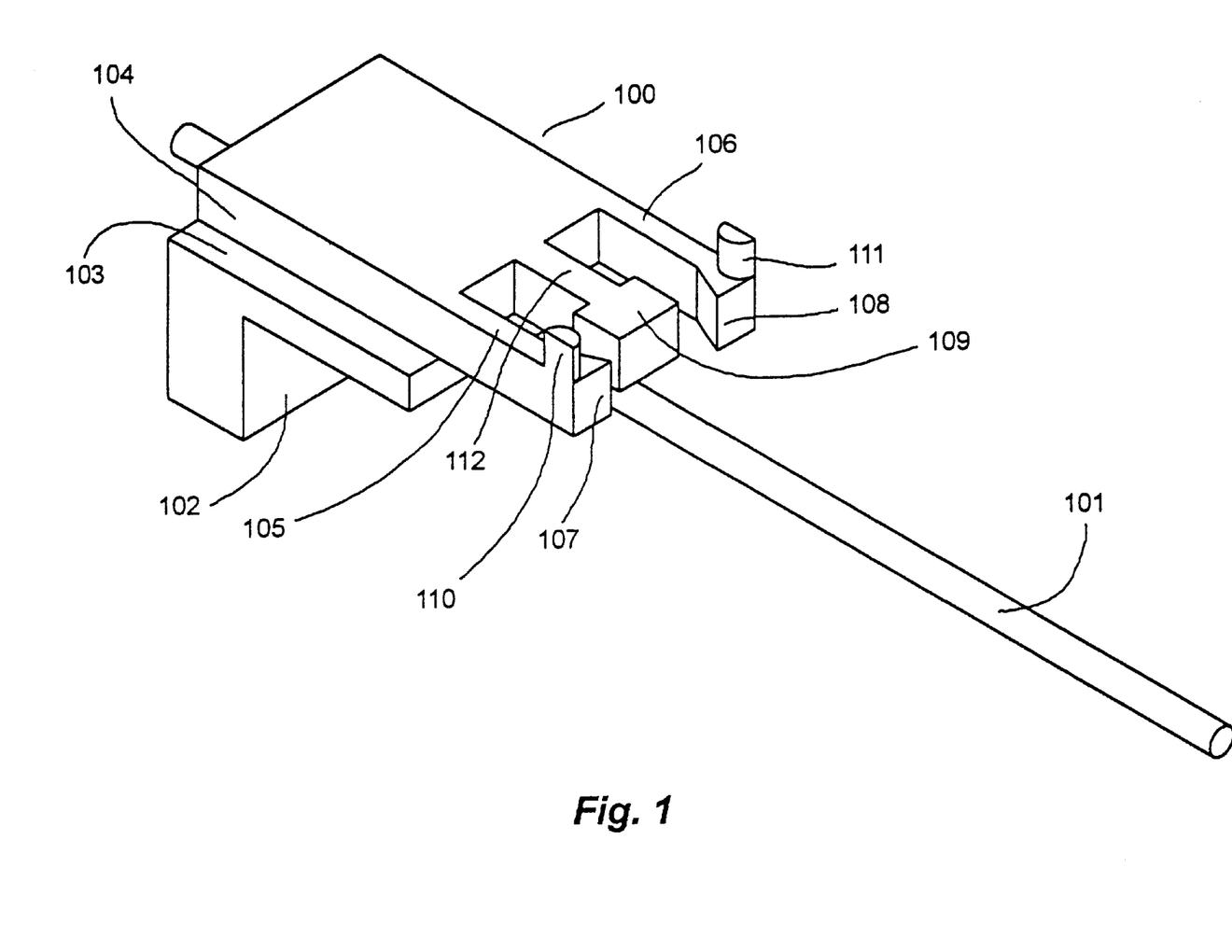
FIG. 1 illustrates a canula with its holder, in a perspective view from a distal viewpoint, only the rear (proximal) portion of the canula being shown.

FIG. 1 shows the rear portion of the canula 101 mounted to its holder 100 by gluing. The flat and substantially rectangular top section of holder 100 has a sturdy and somewhat wider foot section integral with its underside which has a transverse flat impact face 102 facing in a distal direction. By having a width in excess of that of the rectangular top section a pair of upwardly facing slide ways of which only one, 103, is shown are formed on the foot section. The rectangular top section is provided with laterally facing slide ways of which only one, 104 is shown. Slide ways 103 and 104 and their not illustrated counterparts form a pair of mirroring L-shaped guide ways cooperating with a pair of guide rails protruding from opposite sides of the inner wall of a housing (not shown). The front (distal) portion of the top section ends in a pair of slightly flexible arms 105, 106 encompassing a rectangular, wide through-opening into which the neck 112 of a T-formed displacement limiter 109 protrudes from the distally facing rim of the opening. At their free ends the arms 105 and 106 are widening inwardly to form teeth 107, 108 carrying on their upper faces inwardly-rounded stop pins 110, 111 the function of which will be explained below.

Figure 2:
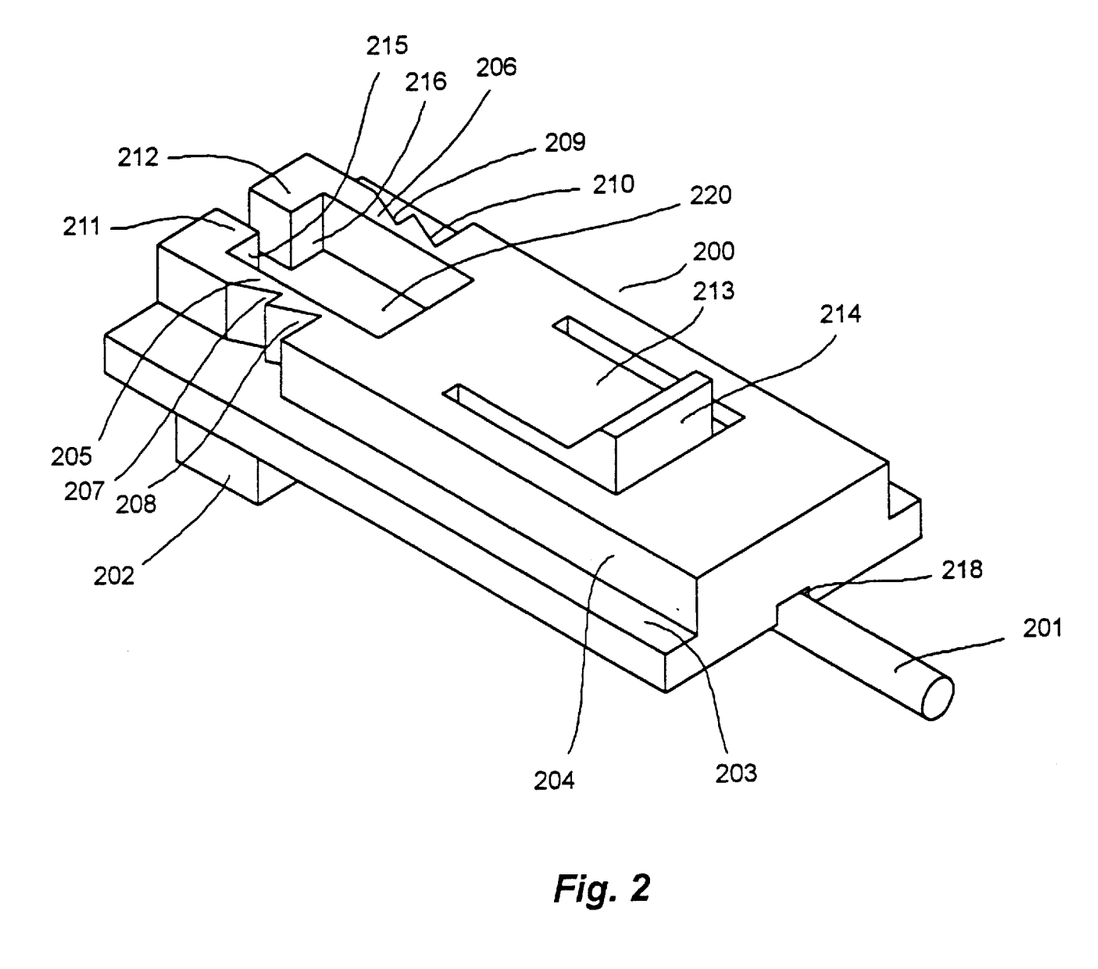
FIG. 2 illustrates a finger tube with its holder, in the same view as in FIG. 1, only the rear (proximal) portion of the finger tube being shown.

FIG. 2 shows the rear portion of the finger tube 201 disposed in a channel 218 of a holder 200 to which it is mounted by gluing. The rear (proximal) end of the finger tube does not protrude from the rear end of the holder 200. The foot section includes a heel 202 and a rectangular base of the same width as the foot section of the canula holder 100. On top of the rectangular base is disposed a substantially rectangular top section. At its rear end the top section includes two arms 205, 206 integral with the base, encompassing a rectangular opening the depth of which is delimited by the top face 220 of the rectangular holder base. The outer (lateral) faces of arms 205, 206 are provided with pairs of indentations 207, 208; 209, 210 for cooperation with teeth 107, 108 of canula holder 100. At their rear free ends arms 205, 206 have inwardly extending hook portions 211, 212 leaving open a passage wide enough to fit around the neck 112 of the displacement limiter. The holder 200 is provided with two pairs of slide ways forming L-shaped guide ways similar to those of holder 100. Of them only one pair, 203; 204 is shown. The left and the right guide ways of holders 100 and 200 are disposed in line. As is evident from FIG. 7 the top section of the holder 200 has a hollow portion distally off arms 205, 206, the top wall of which is cut in the form of a tongue 213. The tip 214 of tongue 213 projects above the upper surface of the top wall. The tongue 213 is somewhat flexible and can be depressed into the hollow space beneath it.

Figure 3:
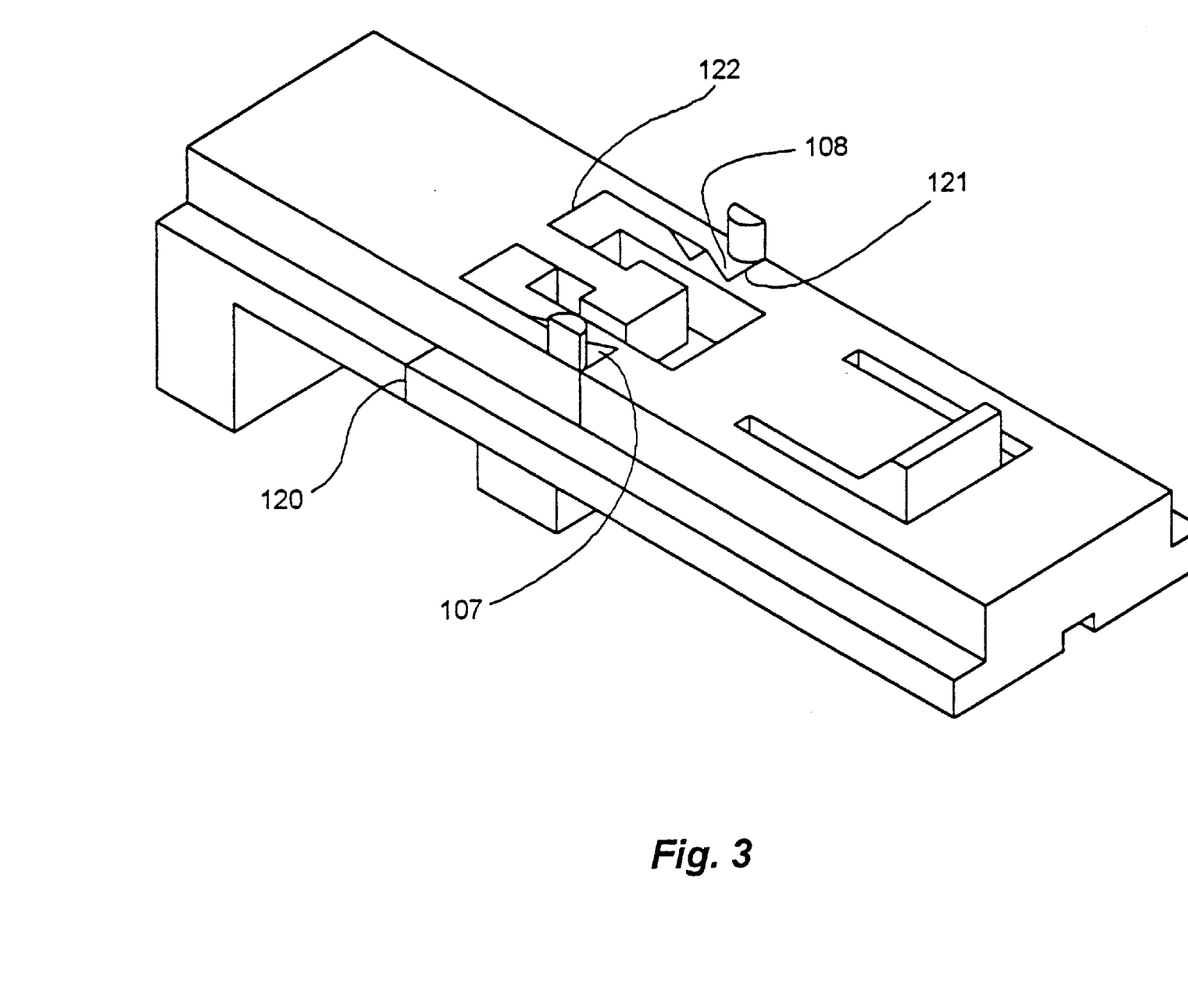
FIG. 3 illustrates the canula and finger tube holders, in a mounted state before and during a first step of an excision procedure, in the same view as in FIGS. 1 and 2.

FIG. 3 shows the canula holder 100 and the finger tube holder 200 in an assembled state before and during the first step in which both travel together. Whereas the canula holder 100 is pushed forward (in a distal direction) by a strong steel coil (not shown; compressed to 70 N) affecting its rear (proximal) end, the finger tube holder 200 is pushed forward by the canula holder 100 with which it is in abutment at 120, 121, 122. Canula holder teeth 107, 108 engage with the respective distal indentation 208, 210 of the finger tube holder 200 to avoid unintended forward movement of the finger tube 201.

Figure 4:
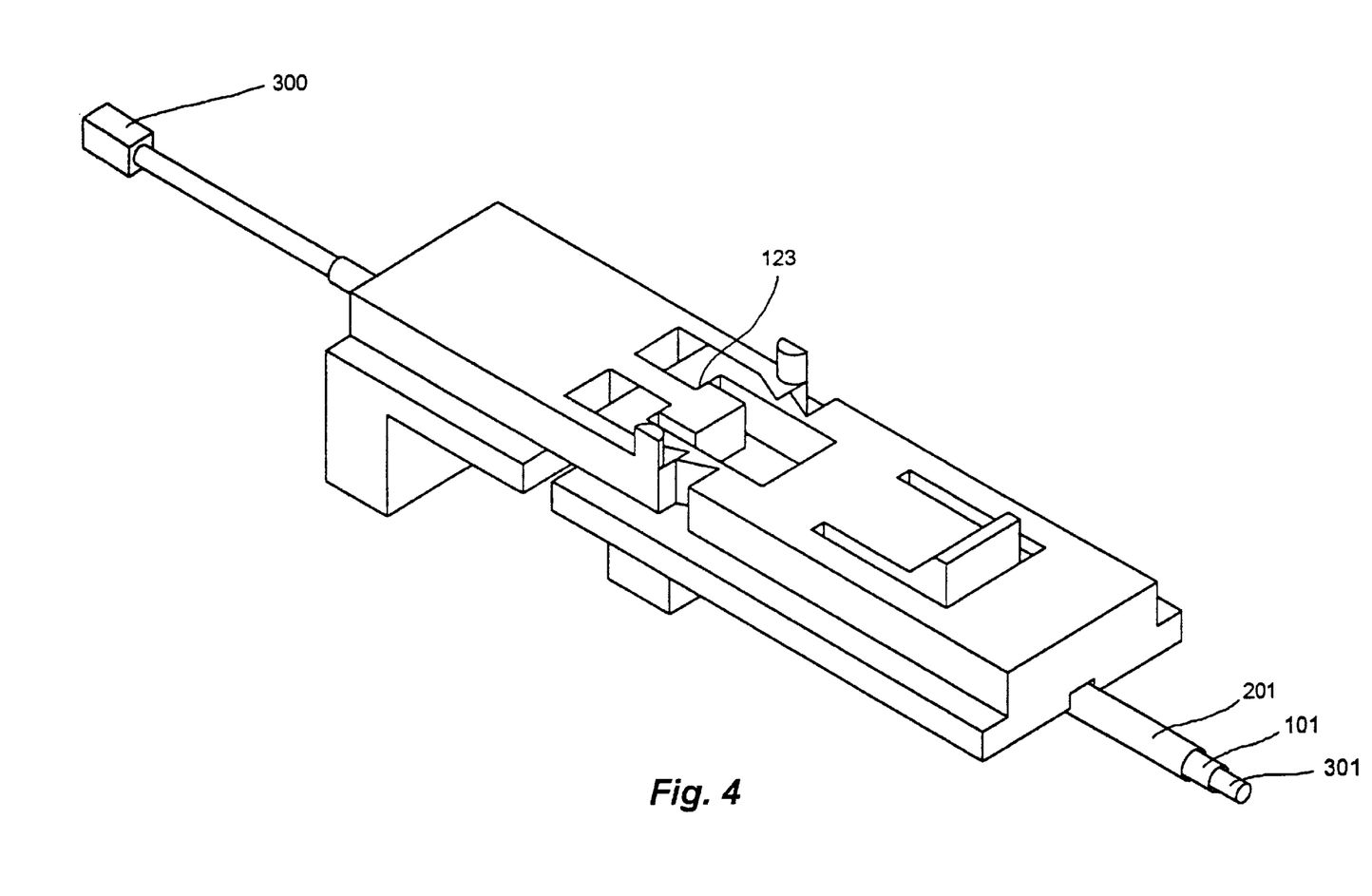
FIG. 4 illustrates the canula, the finger tube, and their respective holders, in a mounted state in the same view as before, at the end of a second step of the excision procedure.

FIG. 4 shows the same arrangement, including cannula 101 and finger tube 201, after the forward travel of canula holder 100 has come to an end while the finger tube holder 200 continues its movement by inertia, only to be stopped by the rear side of the transverse bar of the T-formed displacement limiter 109 abutting faces 215, 216 of hooks 211, 212, respectively. For reasons of balance an additional stop is provided by a front face 221 of the distal heel portion cooperating with a rearward facing wall 415 of the stopper 400 (see below; see FIG. 7 which however illustrates the assembly before or during the joint displacement of the canula 101 and the finger tube 201). In this figure the canula 101, the finger tube 201, and the stylet 301 are shown except for their distal ends. Stylet holder 300 is fixed to the housing (not shown) and thus does not move.

Figure 5:
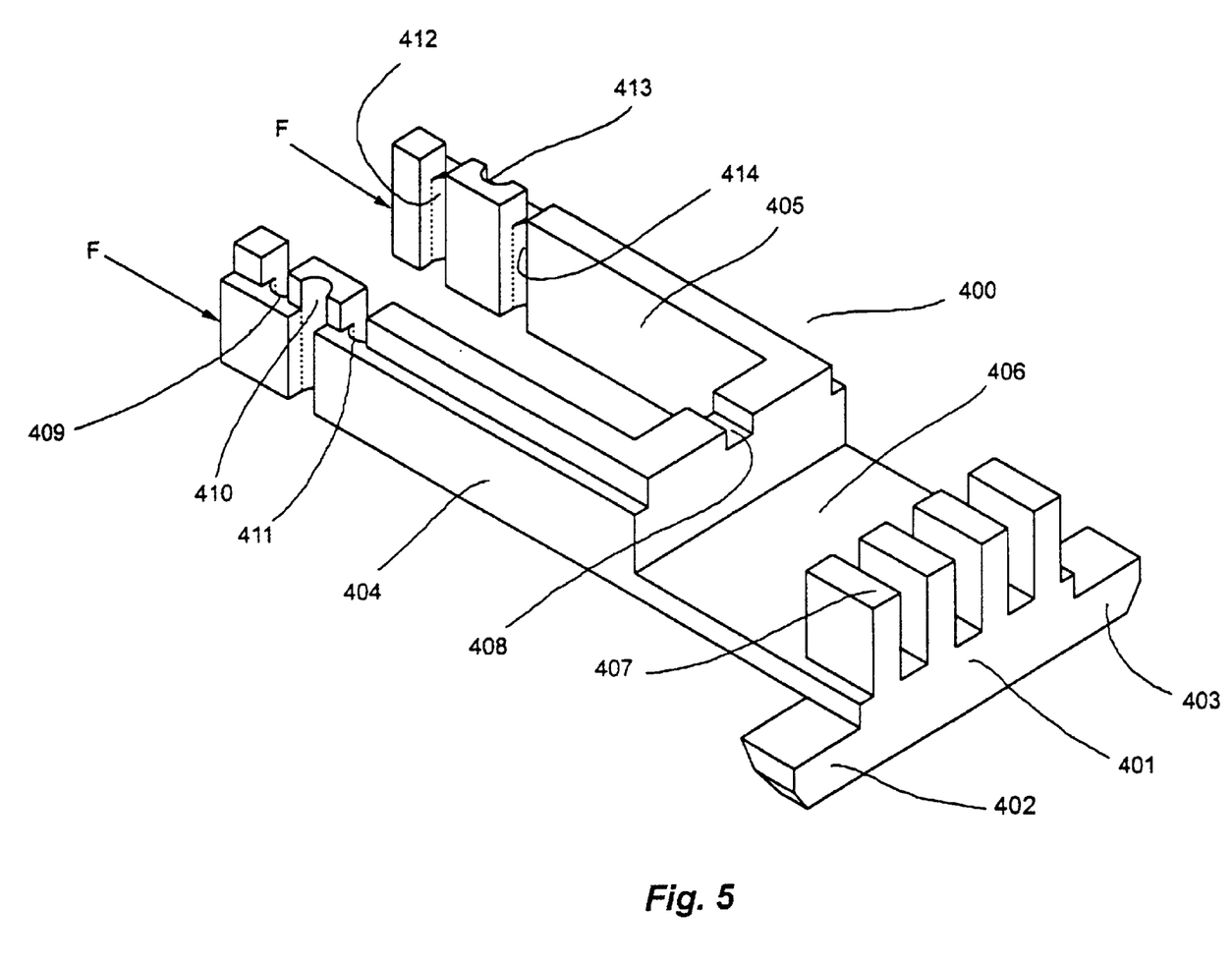
FIG. 5 illustrates a stopper, in the same view as before.

FIG. 5 shows a fork-like stopper 400 for restricting the travel of the canula 101 and the finger tube 201. By arms 402, 403 of the front-end fork shaft handle 401 protruding at opposite sides from the housing (not shown) the stopper 400 can be set at several positions along the canula/stylet axis to select one of a number of predetermined tissue penetration depths. The prongs 404, 405 of the fork are directed rearward to meet the impact (indicated by 'F' in the drawing) of the canula holder (by foot face 102) at their proximal ends.

The impact is damped by hemi-cylindrical recesses 409, 410, 411; 412, 413, 414 alternating at the inner and outer lateral faces of each prong. On impact the prongs 404, 405 are compressed in an axial direction and deformed by a sort of bending due to these recesses. ABS polymers are particularly well suited to the purpose of shock absorbers since they have a high softening point and excellent impact strength as well as a good yield tensile strength (toughness). Advantageously, they combine, by their chemical nature, the good yield tensile strength of general purpose (low impact) polystyrene with the high impact strength of rubbery polymers, such as butadiene rubber. The holders 100, 200, 300 and the stopper 400 are produced by injection molding. In combination with a serpentine geometry of the prong end portions, provision is made for good damping of the oscillatory movement of the canula 101 and the finger tube 201 with their holders 100, 200. With the teaching of the invention in mind the person skilled in the art will be able to produce the damping effect also by modifications of the stopper design other than hemi-cylindrical recesses, for instance by a zigzag design, by bores, etc.

Proper damping (with respect to spring force, etc.) can be determined by experiments in which the depth and/or the number of recesses is varied. In the preferred embodiment according to the invention described above, a steel coil compressed to 70 N was used. The oscillation amplitude of the canula 101 with respect to the finger tube 201 was found experimentally to be in the range from 0.30 to 0.35 mm. In a device identical with that of the invention, except for the hemi-cylindrical recesses 409, 410, 411; 412, 413, 414 which had been omitted, a relative oscillation amplitude of from 1.0 to 1.1 mm was determined experimentally. In this case excessive finger bending or breakage was observed. By using steel coils compressed to a force of 30 N or less oscillation could be kept within acceptable limits.

Between the handle 401, which is provided with stiffening ribs 407, and the prongs 404, 405 the shaft has a flat transitional portion 406 which can be bent to allow the fork shaft handle 401 of the stopper 400 disposed in a latch arranged in the housing wall to be moved in distal/proximal direction between three positions, for instance to latch 503 (see FIG. 8) which position provides for maximal stroke length. The arms 402, 403 of the fork shaft handle 401 protrude through slits at opposite sides of the housing 500 (see FIG. 9) and are thus maneuverable from outside. A central groove 408 cooperates with corresponding channel 218 in the finger tube holder 200 and another one (not shown) in the canula holder 100 is provided for receiving the stylet/canula/finger tip tube assembly.

Figure 6:
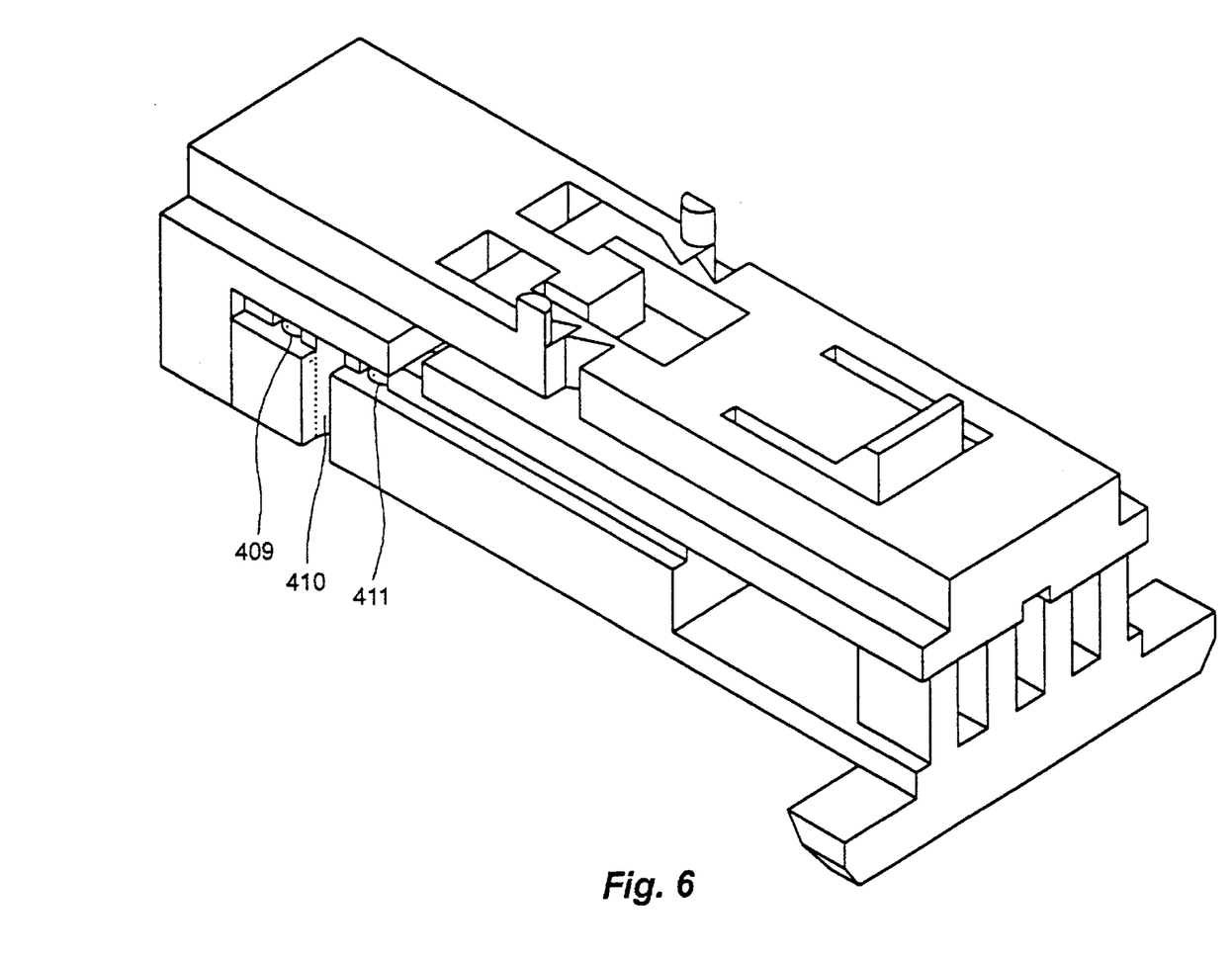
FIG. 6 illustrates the canula holder, the finger tube holder, and the stopper, in a mounted state at the end of the second step, in the same view as before.
Figure 7:
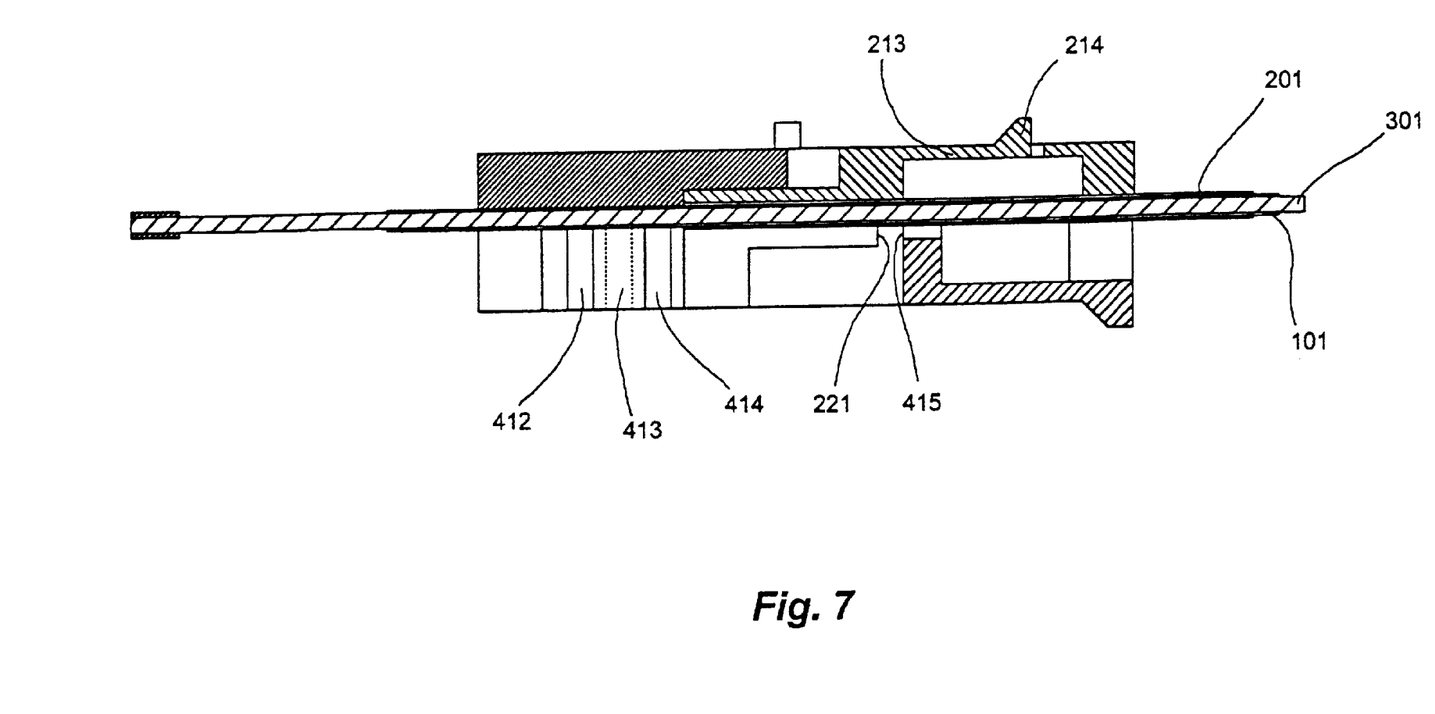
FIG. 7 illustrates the assembly of FIG. 6 before and during the first step, in a symmetric longitudinal section.

In FIG. 6 the stopper 400 is shown mounted with the stylet/canula/finger tube assembly of FIG. 4 at the end of the movement of the finger tube 201. FIG. 7 is a corresponding longitudinal section.

The biopsy apparatus 500 of FIGS. 8–12b incorporates the biopsy instrument of FIGS. 1–7 in a housing 500 consisting of two substantially symmetrical halves sectioned perpendicular to the larger faces of the holders 100, 200 and of the catch 540. Only one half is shown. The housing which has the approximate form of a rectangular bar can be of a suitable polymer, for instance polycarbonate, or of metal, such as aluminum. The housing halves fit by appropriate design of rims 501 and other elements, such as snaps (not shown). The halves can be connected by gluing, welding, or similar process.

Figure 8:
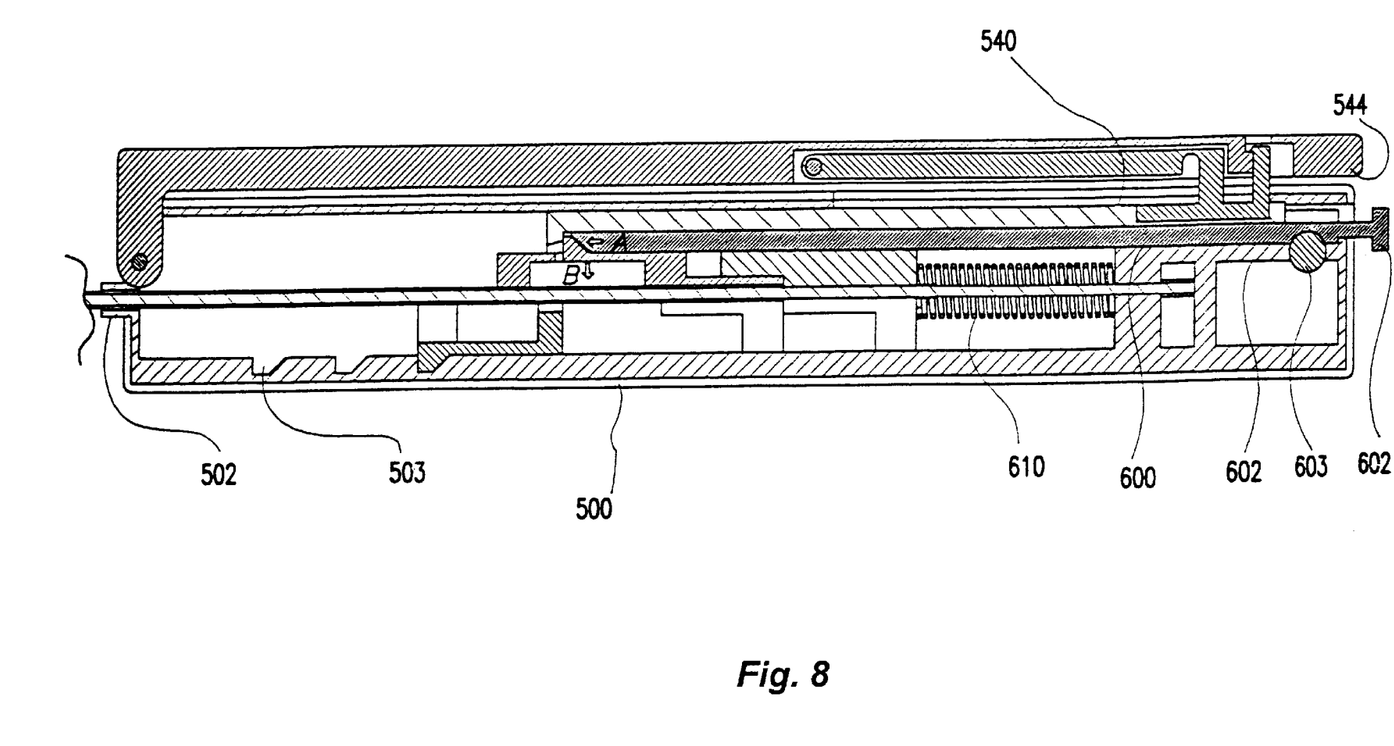
FIG. 8 illustrates a biopsy apparatus incorporating the biopsy instrument of FIGS. 1–7, in a loaded condition and in a symmetric longitudinal section.
Figure 9:
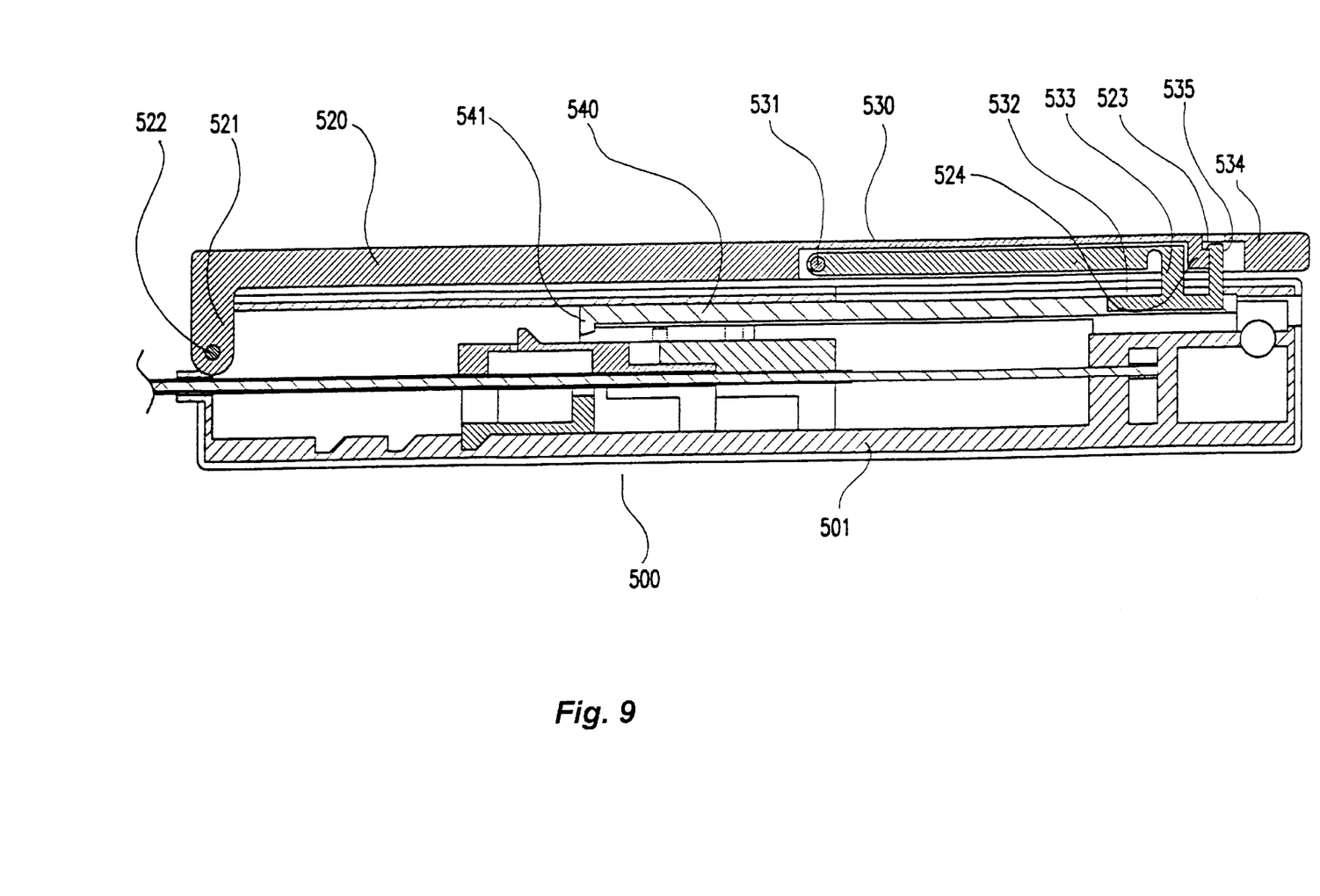
FIG. 9 illustrates the apparatus of FIG. 8, in a released condition at the end of the first step, in the same view as in FIG. 8.
Figure 10:
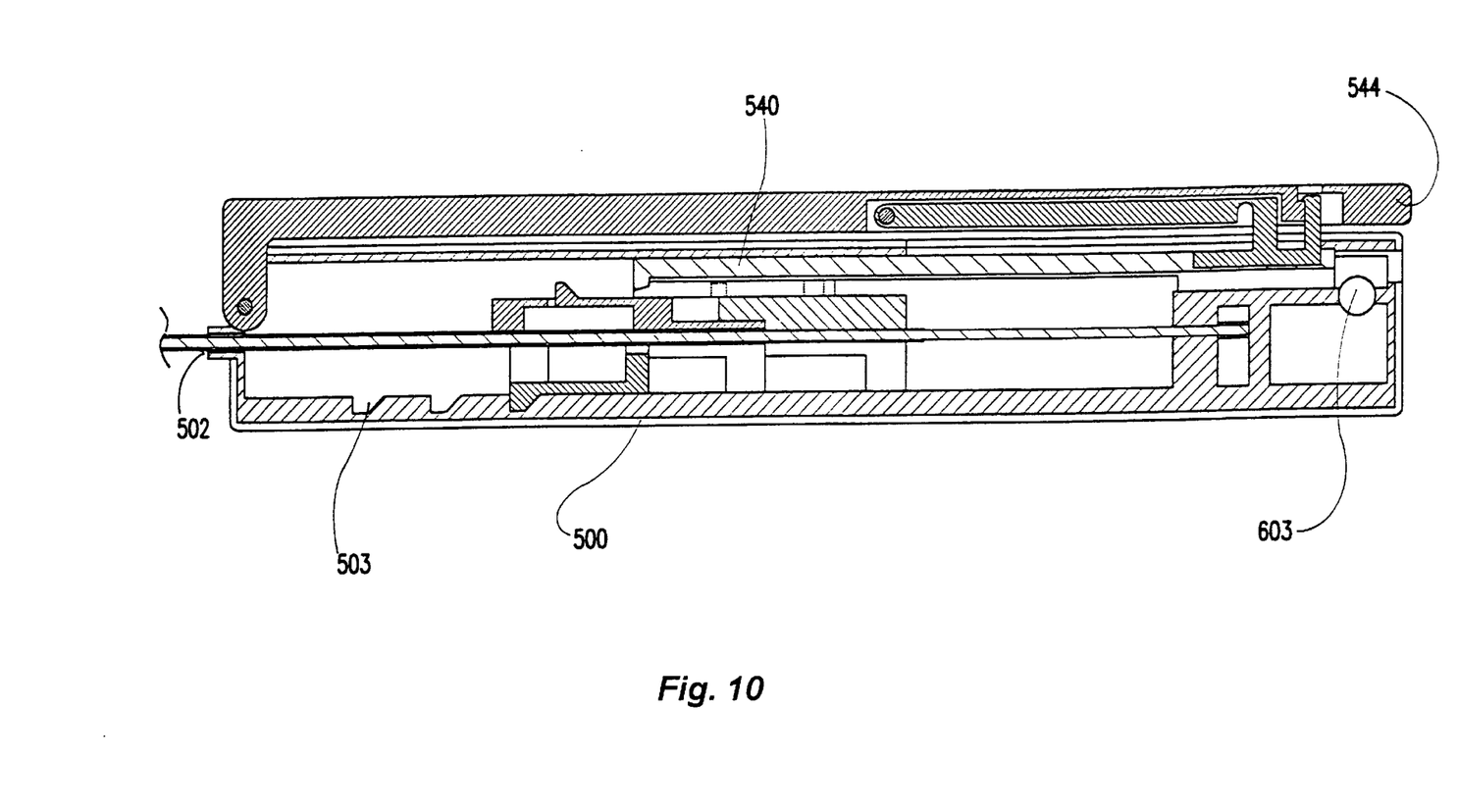
FIG. 10 illustrates the apparatus of FIG. 8, in a released condition at the end of the second step, in the same view as in FIG. 8.
Figure 11:
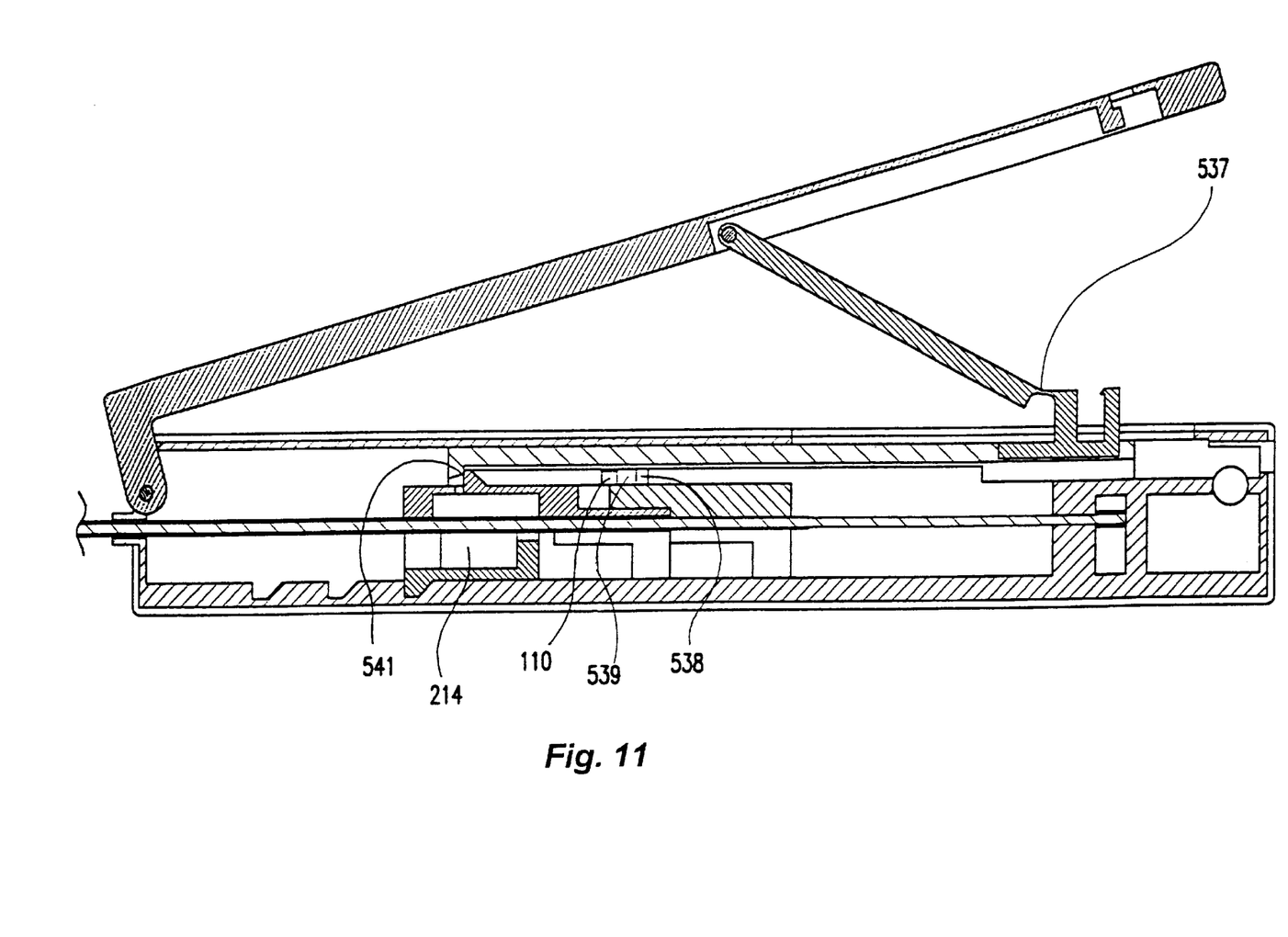
FIG. 11 illustrates the apparatus of FIG. 8, after withdrawal of the finger from the canula but before sample expulsion and loading, in the same view as in FIG. 8.

The holder 300 of stylet 301 is firmly fixed at the housing and can only move with it. The stylet 301, the canula 101 and the finger tube 201, which are disposed substantially centrally in the housing 500 in a distal direction, protrude from the front wall after passage through an opening (at 502) of a diameter slightly greater than the outer diameter of the finger tube 201. The walls of the housing 500 halves have inner profiles functioning as guide rails for holders 100 and 200 which can move forth and back in the housing to the extent permitted by other elements, such as the stopper 400 and the spring 610.

The housing is provided with a loading assembly by which holders 100, 200 are brought to a 'loaded' position from which they can be released for tissue sampling.

To provide for easy loading by which the sturdy spring coil 610 has to be compressed the assembly makes use of three elements: a loading arm 520, an intermediate arm 530, and catch 540 holding the canula holder 100 during compression or in a compressed (loaded) position. With its hook-like front end 541 the catch 540 grips the tip 214 of the finger tube holder's 200 tongue 213, as shown in FIG. 8 where the apparatus is in a loaded state. The canula holder 100 in turn is held in position by some of its front faces abutting rear faces of finger tube holder 200, such as at 120 (FIG. 3).

The canula holder/finger tube holder assembly 100, 200 can be released from the loaded state by an oblong trigger 600 disposed between the catch 540 and canula holder/finger tube holder assembly 100, 200. The rear end of trigger 600 forms a release button 602, which passes through an opening in the rear wall of the housing 500. By pressing the release button 602 the trigger 600 is pushed forward (direction A in FIG. 8), thereby dislocating downwards, by its slanting front end abutting the slanting rear face of tongue tip 214 (direction B in FIG. 8), thereby releasing the canula holder/finger tube holder assembly 100, 200. The biopsy apparatus can be secured in a loaded position by a transversely displaceable locker pin 603 disposed near the rear end of the housing in through-bores of the housing. When inserted the locker pin 603 cooperates with an arc-formed cutout of the trigger 600.

Prior to sampling, the cannula 101 is inserted into the tissue to a depth at which a sample is intended to be collected. Injection is made easy by the use of a canula of small diameter having a thin wall and a sharp cutting edge.

In the first sampling step the canula holder 100 and the finger tube holder 200 are dislocated together in a distal direction until the canula holder foot face 102 hits the rear end of the stopper 400 (at arrow heads F in FIG. 5). In the second sampling step the finger tube holder 200 with the finger tube 201 continues to travel by inertia until stopped by rear faces of the cannula holder (at 123; FIG. 4) and the stopper (at 415; FIG. 7). At the end of the second step (FIG. 10) the finger (not shown) of the finger tube 201 has entered the interior of the canula 101 through a wall opening, thereby cutting off a substantially cylindrical tissue sample disposed in the canula. On withdrawal of the biopsy apparatus the tissue sample remains in the canula and can be recovered.

By pushing the rear end 544 of the loading arm 520 away from the housing 500 the transverse bar 521 of the front end of the L-shaped loading arm 520 is made to swivel around a pivot 522 by which it is fixed at the housing. This releases the rear end of the loading arm 520 from a snap connection made up of a snap hook 535 of the upper transverse bar of an F-formed intermediate arm end portion engaging with a shoulder 524 of the loading arm 520 pertaining to the wall of an opening 523 therein. The vertical bar 532 of the F-shaped intermediate arm 530 portion is slidingly disposed in the housing 500. The lower transverse bar 533 protrudes from the housing 500 through a wide slit extending over a substantial portion of the housing 500 in a distal direction from close its rear end. Near its other end the intermediate arm 530 is fastened to the loading arm 520 rotatably about a link 531. A further joint 537 is provided in the intermediate arm 530 where its straight portion extending from the link 531 is joined to the lower transverse bar 533. This joint 537 is obtained by the provision of a recess which makes the relatively thin (1–2 mm) portion of reduced thickness easy to bend; a flexible polymer, such as polyethylene or nylon, is an appropriate material for the intermediate arm 530.

Figure 12A:
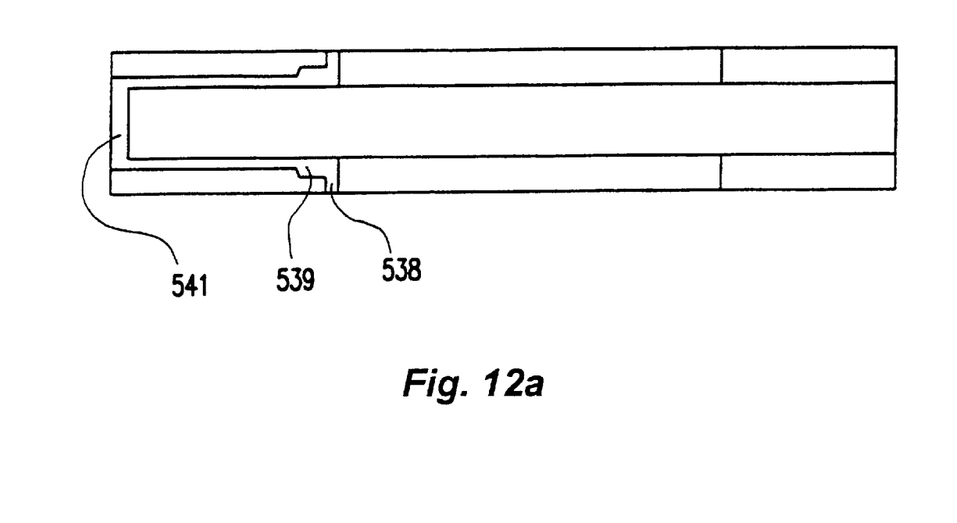
FIG. 12a illustrates the catch of the loading assembly of the apparatus of FIG. 8, in a plan view from above.
Figure 12B:
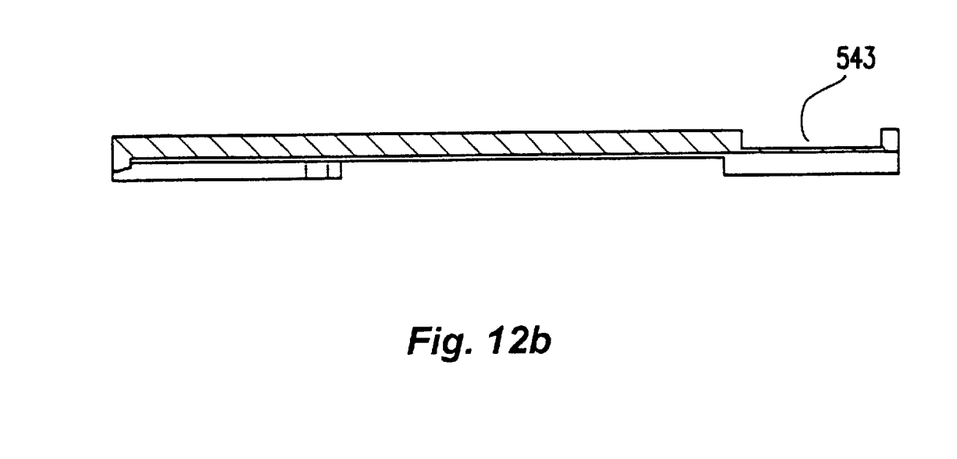
FIG. 12b illustrates the catch of FIG. 12a, in the same view as the apparatus of FIGS. 8–11.

When loading arm 520 is pushed or pulled from the housing 500 the F-shaped intermediate arm portion travels in a distal direction and the catch 540 of which engages a recess 543 (FIG. 12b). The front end hook portion 541 of the catch eventually overrides the tongue tip 214 by forcing it to bend downwards through pressure applied against its slanting rear face. After engagement of the hook portion 541 with the tongue tip 214 further movement of the catch 540 in a distal direction is prevented by the stops 538 on the catch 540 abutting the inwardly rounded stop pins 110, 111 of the canula holder 100. Just before reaching the stops 538 the stop pins 110, 111, and with them the resiliently-flexible arms 105, 106 of the canula holder 100, are pressed outward by shoulders 539 of lateral, outward facing guide walls (FIG. 12a) and remain in that position when abutting stops 538. The catch 540 now has reached its extreme distal position. Further movement of the finger tube holder 200 with respect to the canula holder 100 is prevented by their abutment at 123 (FIG. 4).

Since the shoulders 539 slant slightly inwardly in a direction away from the stops 538, the stop pins 110, 111 with the arms 105, 106 are pressed rearward. Thereby the teeth 107, 108 of the flexible arms 105, 106 disposed in the proximal indentations 208, 210 of finger tube holder arms 205, 206 become disengaged whereby the finger tube holder 200 is unlocked and carried forward until it is stopped by the canula holder 100 while the teeth 107, 108 snap into the distal indentations 207, 209. In FIGS. 8–11 the lines indicating the position of stop pin 110, the shoulder 539, and the stop 538 are dotted.

By carefully moving, in the following step, the loading arm 520 towards the housing 500 the canula 101 and the finger tube 201 are retracted while the sample is expelled by the stylet 301. The biopsy apparatus is now ready for re-loading to prepare it for removal of another sample of tissue. Arm 520 is pressed towards the housing 500 until the hook 535 of the intermediate arm enters the opening 523 of the loading arm 520 and engages the shoulder 524 to form a snap connection. At the same time the free end portion 534 of the intermediate arm 530 moves rearward and compresses the coil spring 610 via intermediate holders 100, 200 of the biopsy instrument. The flat trigger 600 is only active in triggering release and, therefore, has been omitted from the drawings except for FIG. 8.

The construction of the loading assembly is also advantageous in that the loading arm 520 with the apparatus in a loaded position forms a single body with the housing 500 which is comfortable to hold and maneuver, and which is safe. It is also advantageous through its reduction of the force needed for compressing the spring coil. It is obvious to the person skilled in the art that the loading assembly also could be used with a strong tension spring which, for other reasons, however, is not as attractive in the present context as a compression spring.

The person skilled in the art will have no difficulty in modifying the invention by various combinations of its features, for example, without departing from its teaching. Accordingly, the present invention is to be limited not by the description of the preferred embodiments set forth above, but only by the appended claims.

What is claimed is:

1. In combination, a holder and a biopsy instrument comprising a tubular cannula having a cannula bore and with a front end and an axial opening at the front end communicating with the cannula bore, a wall of the cannula having, in proximity of the front end, an opening extending through the wall; a substantially cylindrical tube having a bore and with an axial front end and an opening at the front end communicating with the bore of the tube, the tube having a projection at the front end opening with an end section bent toward the axis of the tube, wherein the cannula is adapted for being disposed in the bore of the tube, and the end section of the tube is shaped for being inserted into the opening in the cannula wall and is axially displaceable in a forward direction so as to be deflected towards the axis of the cannula, a spring exerting a force, and being arranged for displacing the cannula and the cylindrical tube in a distal direction, means for damping to reduce the oscillation of the cannula and the tube relative to each other when displacement is stopped, the canula and the tube including means for connecting them with the holder for axial forward displacement of the cannula and the tube.

2. The holder and biopsy instrument of claim 1, wherein the spring is arranged for substantially consecutive axial displacement of the cannula and tube in combination, and of the tube only.

3. The holder and biopsy instrument of claim 1, wherein the spring comprises a steel coil spring.

4. The holder and biopsy instrument of claim 1, wherein the means for damping to reduce the oscillation of the cannula and the tube relative to each other when displacement is stopped keeps the oscillation of the cannula with respect to the tube within 0.4 mm.

5. The holder and biopsy instrument of claim 1, wherein the force exerted by the spring is at least about 35 N.

6. The holder and biopsy instrument of claim 1, wherein the projection is structured and arranged for contacting an edge of the opening in the wall of the cannula such that the end section is deflected towards the axis of the cannula.

7. The holder and biopsy instrument of claim 1, further comprising a second projection at the front end of the tube and a second opening in the cannula wall.

8. The holder and biopsy instrument of claim 1, further comprising a stylet inserted in the cannula.

* * * * *